United States Patent [19]

Russell

[11] Patent Number: 4,786,732
[45] Date of Patent: Nov. 22, 1988

[54] RESOLUTION OF ENANTIOMERS OF 2-(4-ARYLOXYPHENOXY) PROPIONIC ACIDS BY LIQUID CHROMATOGRAPHY WITH A CHIRAL ELUENT

[75] Inventor: John W. Russell, Midland, Mich.

[73] Assignee: The Dow Chemical Company, Midland, Mich.

[21] Appl. No.: 81,515

[22] Filed: Aug. 5, 1987

[51] Int. Cl.$^4$ .................. C07D 241/36; C07D 211/72; C07B 57/00
[52] U.S. Cl. .................... 544/354; 546/295; 71/92; 71/94; 71/109; 71/116; 560/62; 562/401; 562/472
[58] Field of Search .................. 562/401, 472; 560/62; 544/354; 546/295

[56] References Cited

U.S. PATENT DOCUMENTS

| | | | |
|---|---|---|---|
| 3,954,442 | 5/1976 | Becker et al. | 71/108 |
| 4,332,960 | 1/1982 | Trosken et al. | 560/62 |
| 4,370,489 | 1/1983 | Boesenberg et al. | 560/62 |
| 4,531,969 | 7/1985 | Nestler et al. | 71/108 |
| 4,550,192 | 10/1985 | Rogers et al. | 560/62 |
| 4,565,568 | 1/1986 | Johnston et al. | 71/94 |
| 4,609,396 | 9/1986 | Fawzi | 71/92 |

OTHER PUBLICATIONS

Wainer, *Liquid Chromatography in Pharmaceutical Development: An Introduction*, Aster Publ. Corp. Springfield, Ore., pp. 110–125, (1985).
Wainer, *Chromatography Forum*, 1, (4), 55–61, (1986).
Souter, CRC Press, Boca Raton, Florida, pp. 103, 155, 157, 174, 187, and 189; (1985).
Petterson et al., *Journal of Liquid Chromatography*, 9(2&3), pp. 269–290, (1986).

*Primary Examiner*—Werren B. Lone
*Assistant Examiner*—Vera C. Clarke
*Attorney, Agent, or Firm*—Craig E. Mixan; Ronald G. Brookens

[57] ABSTRACT

A method for the effective chromatographic resolution and analysis of the enantiomers of 2-(4-aryloxyphenoxy)propionic acids which comprises dissolving a 2-(4-aryloxyphenoxy)propionic acid in a suitable solvent, injecting the solution into a liquid chromatographic system and eluting the components from the column using an eluent contain R-(−)- or S-(+)-2-pyrrolidinemethanol and an alkanoic acid in a suitable solvent.

7 Claims, No Drawings

RESOLUTION OF ENANTIOMERS OF 2-(4-ARYLOXYPHENOXY) PROPIONIC ACIDS BY LIQUID CHROMATOGRAPHY WITH A CHIRAL ELUENT

BACKGROUND OF THE INVENTION

The herbicidal activity of 2-(4-aryloxyphenoxy)propionic acids and derivatives thereof is well known in the art. Furthermore, optical isomers are often known to exhibit enhanced herbicidal activity over the corresponding racemates. For example, U.S. Pat. No. 4,531,969 discloses that the R-enantiomers of certain 2-(4-aryloxyphenoxy)propionic acids and certain derivatives thereof are distinguished by a considerably enhanced herbicidal action compared to the racemic modifications. Since reduced quantities of herbicide are required to achieve comparable levels of control, the application of mixtures enriched in the more efficacious R-enantiomer offers both economical and environmental advantages.

In order to commercially exploit the benefits of the advantages associated with the use of the biologically more active enantiomer, it is necessary to accurately determine the ratio of the R- and S-enantiomers in a specific composition. Besides allowing one to monitor the production process, such analytical capability is required to support product labeling and registration requirements. One of the most current approaches to achieving such a resolution and analysis involves the use of chiral mobile-phase additives in liquid chromatography. With this approach, the resolution of enantiomeric compounds can be accomplished by the formation of diastereomeric complexes of the enantiomeric substrate to be resolved and the optically active component added to the eluent. The resolutions are chromatographically effected on the basis of the differences of the diastereomeric complexes formed, e.g., differences in their stabilities, in their solvation in the mobile phase or in their binding to the solid support.

Recently, chiral ion-pairing chromatography has been introduced as a refinement of the above approach. The application of the technique has been extended to enantiomeric carboxylic acids by the addition of naturally-occurring, optically active cinchona alkaloids such as quinine to the mobile phase. The method is based on the formation of diastereomeric amine salts of the carboxylic acid and the optically active cinchona alkaloid.

Although an exceptional resolution of enantiomeric carboxylic acids is possible with this technique, a major drawback is that quinine and related alkaloids are strong ultraviolet absorbers and so provide substantial detector background in the ultraviolet detectors commonly employed in liquid chromatographic analyses. Any slight pressure change, for example, switching an injector valve, upsets the equilibrium causing a baseline excursion. In addition, vacancy chromatography occurs, resulting in inverse peaks, particularly at the retention time for elution of the alkaloid. Consequently, despite exceptional resolution, the procedure is ill-suited to accurate quantitative measurement of enantiomer ratios.

SUMMARY OF THE INVENTION

The present invention provides a method for the effective chromatographic resolution and analysis of the enantiomers of 2-(4-aryloxyphenoxy)propionic acids of formula (I)

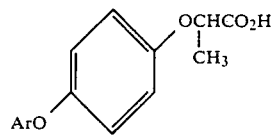

wherein Ar is an unsubstituted or substituted aryl or heterocyclic ring system which comprises dissolving a 2-(4-aryloxyphenoxy)propionic acid of formula I in a suitable solvent, injecting the solution into a liquid chromatographic system and eluting the components from the column using an eluent containing R-(−)- or S-(+)-2-pyrrolidinemethanol and an alkanoic acid in a suitable solvent.

The 2-(4-aryloxyphenoxy)propionic acids to which the present method may be applied are disclosed for example in U.S. Pat. Nos. 3,954,442, 4,332,960, 4,370,489, 4,531,969, 4,550,192, 4,565,568, and 4,609,396 and in European patent applications publication Nos. 0000483 and 0001473.

Particularly valuable examples of 2-(4-aryloxyphenoxy)propionic acids to which the present method may be applied are of formula:

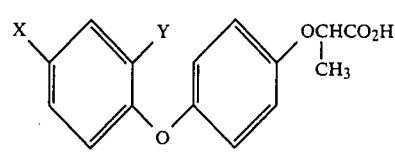

wherein X is $CF_3$, F, Cl, Br, I or $NH_2$ and Y is H, F, Cl, Br or I,

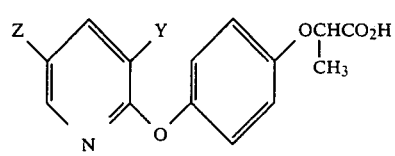

wherein Z is $CF_3$, F, Cl, Br or I and Y is as defined above, and

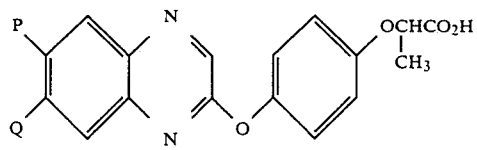

wherein P and Q are independently H, F, Cl, Br or I.

For compounds of formula (II), X is preferably Cl, Br or I and Y is preferably F or Cl.

For compounds of formula (III), Z is preferably $CF_3$, Cl, Br or I and Y is preferably H, F or Cl.

For compounds of formula (IV), one of P or Q is preferably F or Cl.

Suitable solvents for the chromatographic process include those which are capable of dissolving the sample of 2-(4-aryloxyphenoxy)propionic acid, are capable of functioning as the primary constituent of the mobile phase and are free of undesirable ultraviolet absorptions. Preferred solvents include chlorinated hydrocarbon solvents, either alone or in admixture with aliphatic alcohols, with chloroform being particularly desirable.

The commercially available optically active S-(+)- and R-(−)-2-pyrrolidinemethanol enantiomers are particularly well-suited as chiral additives because they lack ultraviolet absorptions typical of the prior art cinchona alkaloids. Both enantiomers are equivalent in their resolving power, but replacement of one for the other results in a reversal in the order of elution of the enantiomer peaks. Since the R-enantiomer of the 2-(4-aryloxyphenoxy)propionic acids is more active and commercial compositions will be advantageously directed to minimizing the S-enantiomer, the use of R-(−)-2-pyrrolidinemethanol is preferred. With this situation, the determination of the impurity enantiomer is facilitated by eluting before the major enantiomer rather than on its tail.

In general, the more optically active 2-pyrrolidinemethanol present, the shorter the retention times, but an optimum concentration exists for obtaining resolution. The optimum concentration varies from system to system but can readily be determined by routine procedures well known to those skilled in the art. Concentrations of optically active 2-pyrrolidinemethanol between $10^{-4}$ and $10^{-2}$ molar are preferred.

In ion-pairing chromatography, a counter ion is necessary. Hence an alkanoic acid is added to the mobile phase in equimolar concentration to the optically active 2-pyrrolidinemethanol. Any lower alkyl carboxylic acid can be used, but $C_1$-$C_4$ alkanoic acids are preferred.

Stationary phases consisting of glyceryl terminated silica or "diol" are the preferred solid supports for the intended separations. Particle sizes may vary from $3\mu$ to $50\mu$ but those of $3\mu$ to $10\mu$ are preferred.

Various eluent flow rates can be used limited by the pressure limitations of the chromatographic system. Optimum flow rates can be readily determined by procedures well known to those skilled in the art.

Prior to operation, equilibrium loading of the optically active pyrrolidinemethanol on the column must be established. This can be initially achieved by feeding the mobile phase to the column for a period of 2 to 3 hours.

Although the present invention resolves only free acids, it can be extended to the $C_1$-$C_4$ alkyl esters of formulas (I-IV) following hydrolysis procedures that are free of undesirable racemization. For example, neat esters can be hydrolyzed by mild heating with 50 percent caustic in a mixture of acetonitrile and water. After neutralization and saturation with sodium chloride, the acid can be isolated by extraction with chloroform. The chloroform extract can be analyzed directly.

In addition, herbicidal formulations of esters containing typical solvents, surfactants, adjuvants, and carriers can be analyzed similarly to the neat esters themselves after appropriate extractive and evaporative workup. With the liquid formulations the cosolvents used for the hydrolysis, e.g., acetonitrile, can be omitted.

Thus, the present invention provides a procedure for the simple and accurate determination of the optical purity of 2-(4-aryloxyphenoxy)propionic acids and the $C_1$-$C_4$ alkyl esters thereof after hydrolysis to the free acids. Furthermore, the procedure can be directly applied to herbicidal formulations of esters following hydrolysis to the free acids. The technique is very simple and avoids the necessity of pre-column derivatization or the use of chiral columns which are subject to degradation or variations from column to column. The separations are of sufficiently high quality to allow the determination of 0.1 percent concentrations of one enantiomer in the presence of the other.

DETAILED DESCRIPTION OF THE INVENTION

The following examples illustrate the invention.

Example 1

A sample (2 mg) of racemic 2-(4-((3-fluoro-5-trifluoromethyl-2-pyridinyl)oxy)phenoxy)propionic acid was dissolved in 2 mL of chloroform and injected into an analytical liquid chromatographic system as follows:

Injector: 10 μL loop
Column: 25 cm × 4.6 mm. ID packed with 5μ diol, 100 Å pore size derivatized silica HPLC phase (obtainable from Chromega)
Eluent: $4.2 \times 10^{-3}$M S-(+)-2-pyrrolidinemethanol (Aldrich) and $4.2 \times 10^{-3}$M acetic acid in chloroform
Flow Rate: 2 mL/min
Detection: Perkin-Elmer LC-75 UV detector at 280 nm; peaks measured by electronic integration The analysis of the racemic sample gave an R/S ratio of 49.9/50.1.

Example 2

A resolved sample (2 mg) of R-2-(4-((3-fluoro-5-trifluoromethyl-2-pyridinyl)oxy)phenoxy)propionic acid having an independently determined R/S ratio of 99.9/0.1 was dissolved in 1 mL of chloroform and injected into an analytical liquid chromatographic system as follows:

Injector: 10 μL loop
Column: 25 cm × 4.6 mm ID 5μ 60 Å diol (Chromega)
Eluent: 0.01M R-(−)-2-pyrrolidinemethanol and 0.01M acetic acid in chloroform
Flow Rate: 2 mL/min
Detection: 280 nm; electronic integration The analysis of the sample gave an R/S ratio of 99.9/0.1.

Example 3

Synthetic mixtures of partially resolved 2-(4-((3-fluoro-5-trifluoromethyl-2-pyridinyl)oxy)phenoxy)propionic acid were generated by combining accurately weighed amounts of the corresponding racemic sample of Example 1 and the resolved sample of Example 2 and melting together at 100° C. until mixed. In some cases, methylene chloride was added to afford mixing. Then 2 mg/mL solutions were prepared and injected under the chromatographic conditions of Example 2. The results are summarized in Table I.

TABLE I

Determination of Enantiomer Ratios of Synthetic 2-(4-((3-fluoro-5-trifluoromethyl-2-pyridinyl)oxy)phenoxy)-propionic acid Samples Using R-(−)-2-pyrrolidinemethanol

| Sample | Known R/S | Determined R/S |
| --- | --- | --- |
| A | 50.00/50.00 | 50.06/49.94 |
| B | 98.84/1.16 | 98.85.1.15 |
| C | 96.89/3.11 | 96.89/3.11 |
| D | 89.90/10.10 | 89.89/10.11 |
| E | 93.80/6.20 | 93.80/6.20 |
| F | 99.65/0.35 | 99.66/0.34 |

TABLE I-continued

Determination of Enantiomer Ratios of Synthetic 2-(4-((3-fluoro-5-trifluoromethyl-2-pyridinyl)oxy)phenoxy)-propionic acid Samples Using R-(−)-2-pyrrolidine-methanol

| Sample | Known R/S | Determined R/S |
|--------|-----------|----------------|
| G      | 99.30/0.70 | 99.33/0.67    |

Example 4

A sample (5 mg) of resolved R-methyl 2-(4-((3-fluoro-5-trifluoromethyl-2-pyridinyl)oxy)phenoxy)propionate having an independently determined R/S ratio of 94.3/5.7 was treated with 70 mg of 50 percent NaOH in 35 mg of acetonitrile and 320 mg of water in a 1-dram vial. The vial was heated at 40° C. with rapid stirring for 1 hour. After cooling, 1 mL of 1M $KH_2PO_4$ was added to neutralize the mixture and the resulting mixture was saturated with NaCl. The aqueous mixture was extracted with 2.5 mL of chloroform and an aliquot of the chloroform layer was analyzed under the chromatographic conditions of Example 2. The sample had an R/S ratio of 94.3/5.7 indicating the absence of racemization during the hydrolysis procedure.

Example 5

A sample of resolved R-methyl 2-(4-((3-fluoro-5-trifluoromethyl-2-pyridinyl)oxy)phenoxy)propionate having an independently determined R/S ratio of 99.8/0.2 was formulated at the 1.75 wt percent level with a formulation matrix consisting of approximately 40 wt percent paraffinic solvent, approximately 38 wt percent aromatic solvent and approximately 20 wt percent surfactants and adjuvants.

A 70 mg sample of the above formulation was treated with 70 mg of 50 percent NaOH in 320 mg of water in a 1 dram vial. The vial was heated at 40° C. with rapid stirring for one hour. After cooling, 1 mL of 1M $KH_2PO_4$ was added to neutralize the mixture and the resulting mixture was saturated with NaCl. The aqueous mixture was extracted with 2.5 mL of chloroform and an aliquot of the chloroform layer was analyzed under the chromatographic conditions of Example 2. The sample had an R/S ratio of 99.7/0.3 indicating the absence of racemization during the hydrolysis of formulations.

Example 6

The 2-(4-aryloxyphenoxy)propionic acids in Table 2, either as the free acid, $C_1$–$C_4$ alkyl ester or as ester formulations, were analyzed by the procedures of the previous examples. The effective resolution of the enantiomers are indicated by the separation factor α which is defined as $(T_2-T_0)/(T_1-T_0)$ where $T_2$ is the retention time of the second eluting enantiomer, $T_1$ is the retention time of the first eluting enantiomer and $T_0$ is the retention time of unretained components.

TABLE 2

Compounds Resolved Using R—(−)-2-Pyrrolidinemethanol

| Structure | Separation Factor, α |
|-----------|----------------------|
| 2,3-diCl-phenyl-O-phenyl-OCH(CH₃)CO₂H | 1.09 |
| 2-F,3-Cl-phenyl-O-phenyl-OCH(CH₃)CO₂H | 1.11 |
| 2-Cl,3-Br-phenyl-O-phenyl-OCH(CH₃)CO₂H | 1.09 |
| 2-F,3-Br-phenyl-O-phenyl-OCH(CH₃)CO₂H | 1.10 |
| 2-F,3-I-phenyl-O-phenyl-OCH(CH₃)CO₂H | 1.11 |
| 2-Cl,3-NH₂-phenyl-O-phenyl-OCH(CH₃)CO₂H | 1.13 |
| 5-CF₃-pyridinyl-O-phenyl-OCH(CH₃)CO₂H | 1.16 |
| 3-Cl,5-CF₃-pyridinyl-O-phenyl-OCH(CH₃)CO₂H | 1.14 |
| 3-F,5-CF₃-pyridinyl-O-phenyl-OCH(CH₃)CO₂H | 1.14 |

TABLE 2-continued

Compounds Resolved Using R—(—)-2-Pyrrolidinemethanol

| Structure | Separation Factor, α |
|---|---|
| 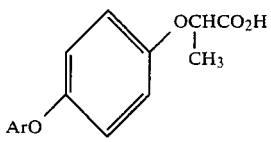 | 1.11 |

Various modifications may be made in the present invention without departing from the spirit or scope thereof, and it is understood that I limit myself only as defined in the appended claims.

What I claim is:

1. A method for the effective chromatographic resolution and analysis of the enantiomers of 2-(4-aryloxyphenoxy)propionic acids of the formula

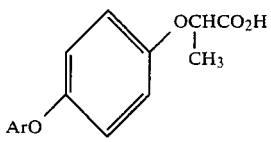

wherein Ar is an unsubstituted or substituted aryl or heterocyclic ring system which comprises dissolving the 2-(4-aryloxyphenoxy)propionic acid in a solvent selected from the group consisting of chlorinated hydrocarbons and admixtures thereof with aliphatic alcohols, injecting the solution into a liquid chromatographic system and eluting the column with an eluent containing R-(—)- or S-(+)-2-pyrrolidinemethanol and an alkanoic acid in said solvent.

2. The method of claim 1 in which the 2-(4-aryloxyphenoxy)propionic acid is of the formula

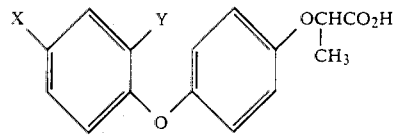

wherein Z is $CF_3$, F, Cl, Br, I or $NH_2$ and Y is H, F, Cl, Br or I.

3. The method of claim 1 in which the 2-(4-aryloxyphenoxy)propionic acid is of the formula

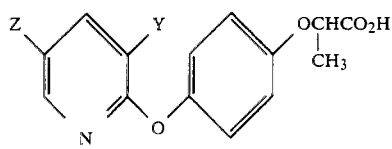

wherein Z is $CF_3$, F, Cl, Br or I and Y is H, F, Cl, Br or I.

4. The method of claim 1 in which the 2-(4-aryloxyphenoxy)propionic acid is of the formula

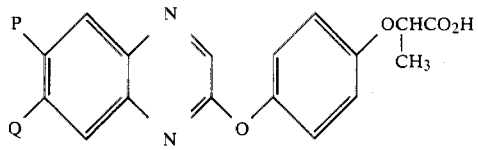

wherein P and Q are independently H, F, Cl, Br or I.

5. The method of claim 1 in which the 2-(4-aryloxyphenoxy)propionic acid is formed without racemization from the corresponding $C_1$-$C_4$ alkyl ester by hydrolysis.

6. The method of claim 5 in which the $C_1$-$C_4$ alkyl ester is present in an agricultural formulation.

7. The method of claim 1 in which the alkanoic acid is acetic acid.

* * * * *